United States Patent [19]

Miyano et al.

[11] Patent Number: 4,831,049

[45] Date of Patent: May 16, 1989

[54] PYRROLIZIDINE COMPOUNDS, AND THEIR USE AS ANTIARRHYTHMIC AGENTS

[75] Inventors: Seiji Miyano, Fukuoka; Kunihiro Sumoto, Oonojo; Fumio Satoh, Nagaokakyo, all of Japan

[73] Assignee: Suntory Limited, Osaka, Japan

[21] Appl. No.: 751,797

[22] Filed: Jul. 3, 1985

[30] Foreign Application Priority Data

Jul. 6, 1984 [JP] Japan .................. 59-141177

[51] Int. Cl.$^4$ .................. C07D 487/04; A61K 31/395
[52] U.S. Cl. ..................... 514/413; 548/453
[58] Field of Search ......... 548/453; 514/413

[56] References Cited

U.S. PATENT DOCUMENTS

| 4,020,094 | 4/1977 | Nelson et al. | 548/528 |
| 4,564,624 | 1/1986 | Miyano et al. | 548/453 |
| 4,617,401 | 10/1986 | Miyano et al. | 548/453 |

FOREIGN PATENT DOCUMENTS

| 0039903 | 11/1981 | European Pat. Off. | 548/453 |
| 0089061 | 9/1983 | European Pat. Off. | 548/453 |
| 0085888 | 5/1983 | Japan | 548/453 |

Primary Examiner—David B. Springer
Attorney, Agent, or Firm—Burgess, Ryan and Wayne

[57] ABSTRACT

A novel pyrrolizidine compound of the formula

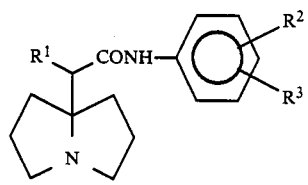

wherein $R^1$ is an alkyl group of 1 to 4 carbon atoms or a phenyl group; and $R^2$ and $R^3$ are such that at least one of them is an alkyl group of 1 to 4 carbon atoms and the other, if not alkyl, being a hydrogen atom is produced by reacting $\Delta^{4(8)}$-dehydropyrrolizidine with a substituted malonic acid and the thus formed 2-substituted-8-pyrrolizidineacetic acid with a substituted aniline. The products are subjected to optical resolution and are potent antiarrhythmic agents.

10 Claims, No Drawings

PYRROLIZIDINE COMPOUNDS, AND THEIR USE AS ANTIARRHYTHMIC AGENTS

This invention relates to novel pyrrolizidine compounds, a method of producing them, and uses thereof.

More particularly, this invention relaes to novel pyrolizidine compounds of the formula (I)

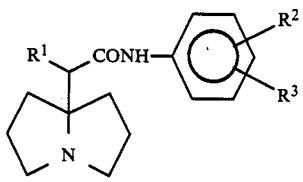

(wherein $R^1$ is an alkyl group of 1 to 4 carbon atoms or a phenyl group; and $R^2$ and $R^3$ are such that at least one of them is an alkyl group of 1 to 4 carbon atoms and the other, if not alkyl, being a hydrogen atom), a method of producing said compound (I), and an antiarrythmic drug containing said compound (I).

Studies on synthesis of 8-substituted pyrrolizidine compounds began with the successful synthesis of 8-hydroxymethylpyrrolizidine and 8-chloromethylpyrrolizidine by N. J. Leonard et al. [J. Am. Chem. Soc., Vol. 71, pp. 1762-1764 (1949)]. Then, Miyano et al. established a method for synthesizing $\Delta^{4(8)}$-dehydropyrrolizidinium perchlorate [Synthesis, pp. 701-702, September, (1978)] which made it possible to synthesize a variety of derivatives in large quantities. Pharmacological investigations were conducted on these compounds and such activities as antiulcer activity, analgesic activity, vasodilating activity and antiarrhythmic activity have been found in these derivatives. (Refer to Japanese Patent Application Kokai Nos. 156283/1981, 85888/1983, 83694/1983, 159493/1983 and 39199/1984).

Particularly, 8-substituted pyrrolizidine derivatives disclosed in Japanese Patent Application Kokai No. 195493/1983 have potent antiarrhythmic activity and than clinical application is being explored.

The present inventors conducted research for the purpose of finding compounds which are more potent in antiarrhythmic activity. As a result of the research, novel 8-substituted pyrrolizidine compounds having desired activity were discovered.

One aspect of this invention is directed to pyrrolizidine compounds of the formula (I)

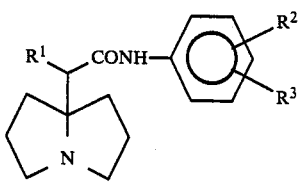

(wherein $R^1$ is an alkyl group of 1 to 4 carbon atoms or a phenyl group; and $R^2$ and $R^3$ are such that at least one of them is an alkyl group of 1 to 4 carbon atoms and the other, if not alkyl, being a hydrogen atom).

Other aspect of this invention is directed to a method of producing pyrrolizidine compounds which comprises reacting $\Delta^{4(8)}$-dehydropyrrolizidine of the formula

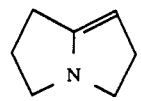

with a substituted malonic acid of the formula

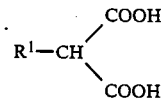

(wherein R' is a lower alkyl group of 1 to 4 carbon atoms or a phenyl group) to give a 2-substituted-8-pyrrolizidineacetic acid of the formula

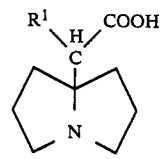

(wherein $R^1$ is as defined above) and reacting the pyrrolizidine-acetic acid compound with a substituted aniline of the formula

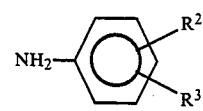

(wherein $R^2$ and $R^3$ are such that at least one of them is an alkyl group of 1 to 4 carbon atoms, and the other, if not alkyl, being a hydrogen atom) to give a N-substituted phenyl-2-(8-substituted pyrrolizidine)substituted acetamide of the formula (I), which is optionally further subjected to optical resolution.

A further aspect of this invention is directed to an antiarrhythmic agent containing a compounds of the formula (I).

The compounds of this invention may be produced by the following method.

Thus, $\Delta^{4(8)}$-dehydropyrrolizidine and a substituted malonic acid are heated in a comparatively high-boiling solvent such as dioxane at 100° to 150° C. for several hours, whereby a 2-substituted-8-pyrrolizidineacetic acid is easily produced as shown in the following scheme;

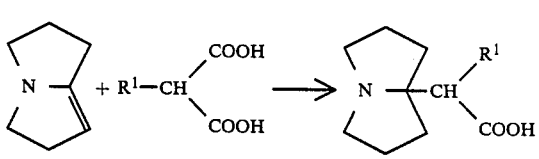

(wherein $R^1$ is as defined hereinbefore).

This pyrrolizidineacetic acid and a substituted aniline are heated in a solvent such as methylene chloride, chloroform, benzene or toluene in the presence of a dehydrating agent such as phosphorus oxychloride or thionyl chloride at 50° to 100° C. for several hours to give a N-substituted phenyl-2-(8-substituted pyrrolizidine) substituted acetamide, as shown in the following scheme;

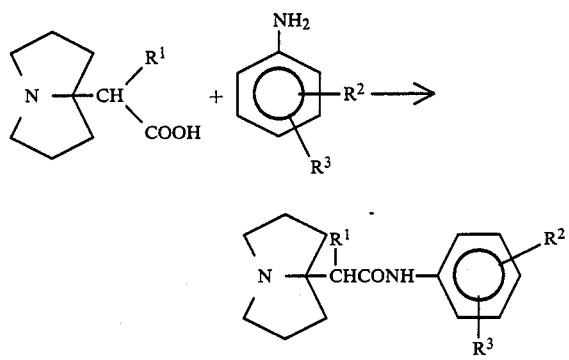

(wherein R¹, R² and R³ are as defined hereinbefore).

This N-substituted phenyl-2-(8-pyrrolizidine) substituted acetamide is a racemic compound which can be directly used in therapeutic applications. However, a compound with a higher safety margin can be produced by subjecting the racemic compound to optical resolution.

For the optical resolution, the racemate is reacted with an optically active tartaric acid or its derivative, such as dibenzoyl tartarate, ditoluoyl tartarate in an alcoholic solvent such as methanol, ethanol or propanol, acetone, or a mixture of said alcohol and acetone to produce a salt, which is then subjected to fractional recrystallization to give an optically active salt. This salt is dissolved in a suitable solvent such as methylene chloride or chloroform and treated with an alkaline solution to give the free (2R)−(−) compound. On the other hand, the (2S)−(+) compound can be similarly obtained from the fractional recrystallization mother liquor.

The amide compound thus obtained is a novel compound which has antiarrhythmic activity as shown below.

Antiarrhythmic activity

In accordance with the method described by J. W. Lawson [Journal of pharmacology and Experimental Therapeutics, 160, 22, (1966)], male mice of ddy strain were caused to inhale chloroform and when respiration was arrested, electrocardiography was performed to observe the ventricular flutter and fibrillation. These abnormalities of the cardiac ventricle are prevented if an antiarrhythmic agent is previously administered. Several different doses of the compound of this invention were subctaneously administered to mice in group of 29 to 40 animals and, after an interval of 30 minutes, the animals were caused to inhale chloroform. The prophylactic effects of these doses on ventricular flutter and fibrillation were estimated and the 50% effective dose ($ED_{50}$) and its 95% confidence limit were calculated by the method of Litchfield and Wilcoxon [Journal of Pharmacology and Experimental Therapeutics 96, 99, (1949)]. The results are shown in Table 1.

The 50% lethal dose ($LD_{50}$) value was determined by the up and down method [Takagi and Ozawa (ed.), Yakubutsu Gaku Jikken, 204, Nanzando, (1972)] based on the data generated in male mice with bodyweights 18 to 22 g. The therapeutic index, which is the ratio of $LD_{50}$ to $ED_{50}$ is also shown in Table 1.

TABLE 1

| Compound | Antiarrhythmic activity $ED_{50}$ mg/kg (95% confidence limit) | $LD_{50}$ mg/kg | Therapeutic |
|---|---|---|---|
| SUN4272 | 115.0 (80.4–164.6) | 400 | 3.4 |
| SUN3341 | 23.0 (14.4–36.8) | 92.1 | 4.0 |
| (2R)−(−)SUN3341 SUN3414 | 2.6 (1.3–5.1) | 67.6 | 26.0 |
| (2S)−(+)-SUN3341 SUN3415 | 24.0 (11.4–50.8) | 79.3 | 3.3 |

TABLE 1-continued

| Compound | Antiarrhythmic activity ED$_{50}$ mg/kg (95% confidence limit) | LD$_{50}$ mg/kg | Therapeutic |
| --- | --- | --- | --- |
| 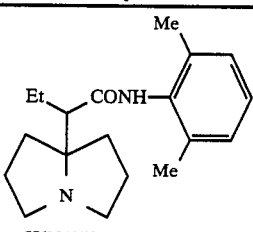 SUN4273 | 8.5 (5.1–14.1) | 26 | 3.1 |
| 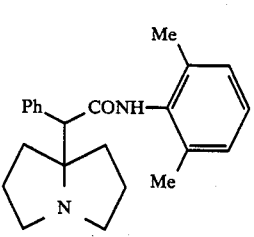 SUN4274 | 3.1 (1.9–5.2) | 22 | 7.1 |

It is apparent from the table that while the compounds of this invention generally have antiarrhythmic activity, the [−]-compound obtained by optical resolution of the racemic compound [(±)-compound] has antiarrhythmic activity as high as approximately 9 times and is comparable to the racemic compound in toxicity, thus giving a remarkably improved therapeutic index.

The compounds according to this invention are used as a therapeutic agent for arrhythmia in the free form or in the form of a pharmaceutically acceptable salt. It can be administered orally or otherwise in appropriate dosage forms such as capsules, tablets, injections, etc., either as it is alone or in combination with the known harmless excipients, vehicles or carriers. Such pharmaceutical preparations can be produced for example by the following procedure. The bulk compound is finely divided, mixed with an excipient such as lactose, starch or a starch derivative, a cellulose derivative, or the like and filled into gelatin capsules to provide capsules. Tablets can be produced as follows. In addition to the above excipient, a binder such as carboxymethylcellulose sodium, alginic acid, gum arabic or the like and water are added to the bulk and the mixture is milled and granulated using an extrusion granulating machine. To the granules so obtained is added a lubricant such as talc, stearic acid or the like and the composition is tableted by means of a conventional tableting compression machine.

For parenteral administration by injection, a water-soluble salt of the compounds of this invention are dissolved in sterile distilled water or sterile physiological saline and the solution is sealed into an ampules. If necessary, a stabilizer or/and a buffer substance may be incorporated.

While the effective dose of any anitarrhythmic agent depends on the type and severity of arrhythmia and the patient's physical factors, it is generally administered in a sufficient amount to restore the abnormal rhythm to the normal rhythm. In regard to the compound of this invention, generally 5 to 200 mg per dose for an adult is administered orally 3 to 4 times daily or 0.05 to 5 mg/kg (body weight) parenterally by intravenous drip infusion.

EXAMPLE 1

Process for production of 2-(8-pyrrolizidine)propionic acid $\Delta^{4(8)}$-Dehydropyrrolizidine perchlorate (20.85 g, 0.1 mole) is treated with 200 ml of ether and 25 l of a 20% aqueous solution of sodium hydroxide. The resulting base (amine) and 11.8 g (0.1 mole) of methylmalonic acid are dissolved in 100 ml of dioxane. The solution is refluxed at 130° C. for 5 hours. The solvent is distilled off and the oily residue is dissolved in acetone. To the solution, ether is added and the mixture is allowed to stand, whereby 10.73 g of slightly hygroscopic crystals are obtained.

Similarly, 2-(8-pyrrolizidine)butyric acid can be obtained in a yield of 7.54 g.

Elemental analysis (%): $C_{11}H_{19}NO_2$: Calcd.: C 66.97, H 9.71, N 7.10. Found: C 67,03, H 9.85, N 7.16.

In a similar manner, 8-pyrrolizidinephenylacetic acid can be obtained in a yield of 5.87 g.

Elemental analysis (%): $C_{15}H_{19}NO_2$: Calcd.: C 73.44, H 7.81, N 5.71. Found: C 73.52, H 7.73, N 5.76.

EXAMPLE 2

Process for producing N-(2,6-dimethylphenyl)-2-(8-pyrrolizidine)propionamide

In 100 ml of chloroform are dissolved 6.63 g (36.2 mM) of 2-(8-pyrrolizidine)propionic acid and 5.26 g (43.44 mM) of 2,6-xylidine. Then, 4.22 g (27.49 mM) of phosphorus oxychloride is gradually added dropwise to the above solution. The mixture is heated for 6.5 hours. The reaction mixture is poured in a cold 5% aqueous solution of sodium hydroxide and the organic layer is separated. The aqueous layer is extracted with chloroform and the chloroform layer are combined, washed with water, dried (MgSO$_4$) and distilled to remove the solvent. The solid residue is recrystallized from acetone-hexane to give 6.43 g (62%) of colorless needles melting at 164°–165° C.

Elemental analysis (%): $C_{16}H_{26}O.\frac{1}{2}H_2O$: Calcd.: C 73.19, H 9.21, N 9.48. Found: C 72.86, H 8.93, N 9.47.

EXAMPLE 3

Process for producing
N-(4-methylphenyl)-2(8-pyrrolizidine)propionamide

Using 3.66 g (20 mM) of 2-(8-pyrrolizidine)propionic acid, 2.6 g (24 mM) of p-toluidine, 2.15 g (14 mM) of phosphorus oxychloride and 100 ml of chloroform, otherwise the same reaction as Example 2 is conducted to give 5.64 g of oil. This oil is treated in methanol with ether saturated with hydrochloric acid to give the hydrochloride and, then, recrystallized from ethanol-ether to give 5.47 g (89%) of colorless needles melting at 220°–221° C.

Elemental analysis (%): $C_{17}H_{24}N_{2L}$ O.HCl: Calcd.: C 66.11, H 8.16, N 9.07. Found: C 65.88, H 8.81, N 9.33.

EXAMPLE 4

Processing for producing
N-(2,6-dimethyl)-2-8-pyrrolizidine)butylamide

The above reaction is carried out using 1.95 g (10 mM) of 2-(8-pyrrolizidine)buryric acid, 1.47 g (12 mM) of 2,6-xylidine and 50 ml of chloroform to give 1.35 g (45%) of colorless needles melting at 183° C. The hydrochoride of this compound occurs as colorless needles melting at 270° C. (decompn.)

Elemental analysis (*): $C_{19}H_{28}N_2O.HCl$: Calcd.: C 67.73, H 8.68, N 8.32. Found: C 67.78, H 8.72, N 8.65.

EXAMPLE 5

Process for producing
N-(2,6-dimethylphenyl)-2-(8-pyrrolizidine)phenylacetamide

The same reaction as above is carried out using 1.5 g (6.55 mM) of 8-pyrrolizidinephenylacetic acid, 0.95 g (7.8 mM) of 2,6-xylidine, 1.0 g (6.5 mM) of phosphorus oxychloride and 50 ml of chloroform to give a solid product. Recrystallization of this product gives 630 mg (25%) of colorless needles melting at 222°–224° C.

Elemental analysis (%): $C_{23}H_{28}N_2.HCl$: Calcd.: C 71.26, H 7.49, N 7.28. Found: C 71.74, H 7.78, N 7.45.

EXAMPLE 6

Optical resolution of
(±)-N-(2,6-dimethylphenyl)-2-(8-pyrrolizidine)propionamide In 150 ml of acetone are dissolved 6.43 g (22.45 mM) of (±)-N-(2,6-dimethylphenyl)-2-(8-pyrrolizidine)-propionamideand 8.67 g (22.45 mM) of di-p-toluoyl-L-(±)-tartaric acid and the solution is allowed to stand at room temperature for 24 hours. The resulting needles (7.76 g, 51.4%) are recovered by filtration, leaving the filtrate (A).

Recrystallization of the crystals gives 6.28 g (41.6%) of colorless needles melting at 167°–167.5° C.

Elemental analysis (%): $C_{33}H_{44}N_2O_3$: Calcd.: C 67.84, H 6.59, N 4.16. Found: C 67.90, H 6.55, N 4.10.

The above crystals are dissolved in chloroform and the di-p-toluoyltartaric acid is removed by washing with a 2% aqueous solution of sodium hydroxide. After drying, the chloroform is distilled off to recover crystals. Recrystallization from acetone gives 2.01 g (31.3%) of colorless needles melting at 169.5°–171° C.

Optical rotation $[\alpha]_D^{25} -32.7$ (c=1, EtOH).

Elemental analysis (%): $C_{18}H_{26}N_2O$: Calcd.: C 75.48, H9.15, N 9.78. Found: C 75.25, H 9.15, N 9.70.

X-ray crystallographic analysis reveals that the configuration at 2-position is R-oriented.

From the filtrate (A) obtained above, the solvent is distilled off to give 7.55 g of pale yellow amorphous powder. This product is converted to the free amine using chloroform and 2% NaOH in the same manner as above and recrystallized from acetone to give 1.49 g (23.2%) of colorless needles melting at 169°–171° C.

Optical rotation $[\alpha]_D^{25} +34.3°$ (c=1, EtOH).

Elemental analysis (%): $C_{18}H_{26}N_2O$: Calcd.: C 75.48, H 9.15, N 9.78. Found: C 75.28, H 9.19, N 9.79.

It is apparent that the configuration at 2-position of this product is S-oriented.

We claim:

1. A pyrrolizidine compound of the formula

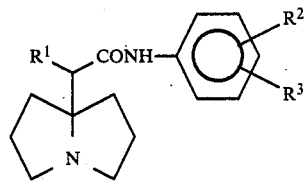

wherein $R^1$ is an alkyl group of 1 to 4 carbon atoms or a phenyl group; and $R^2$ and $R^3$ are such that at least one of them is an alkyl group of 1 to 4 carbon atoms and the other, if not alkyl, being a hydrogen ato and optically active isomers thereof.

2. A pyrrolizidine compound according to claim 1, which is N-(2,6-dimethylphenyl)-2-(8-pyrrolizidine)-propionamide, N-(4-methylphenyl)-2-(8-pyrrolizidine)-propionamide, N-(2,6-dimethylphenyl)-2-(8-pyrrolizidine)butylamide or N-(2,6-dimethylphenyl)-2-(8-pyrrolizidine)phenylacetamide, or an optically active isomer thereof.

3. An antiarrhythmic agent containing as an active ingredient a pyrrolizidine compound of the formula

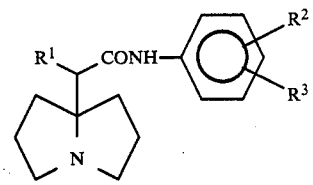

(wherein $R^1$ is an alkyl group of 1 to 4 carbon atoms or a phenyl group; and $R^2$ and $R_3$ are such that at least one of them is an alkyl group of 1 to 4 carbon atoms, with the other, if any, being a hydrogen atom and optically active isomers thereof).

4. An antiarrhythmic composition according to claim 3 wherein said pyrrolizidine isomer is an optically active compound.

5. A pyrrolizidine compound according to claim 1, which is N-(2,6-dimethylphenyl)-2-(8-pyrrolizidine)-propionamide, or an optically active isomer thereof.

6. A pyrrolizidine compound according to claim 1, which is N-(4-methylphenyl)-2-(8-pyrrolizidine)propionamide, or an optically active isomer thereof.

7. A pyrrolizidine compound according to claim 1, which is N-(2,6-dimethylphenyl)-2-(8-pyrrolizidine)-butylamide, or an optically active isomer thereof.

8. A pyrrolizidine compound according to claim 1, which is N-2,6,-dimethylphenyl)-2-(8-pyrrolizidine)-phenylacetamide, or an optically active isomer thereof.

9. A method for producing an antiarrhythmic effect in a patient exhibiting arrhythmia which comprises administering to said patient an antiarrhythmically effective amount of the composition of claim 5.

10. The method of claim 9 wherein said composition is administered orally in dosage amounts of said active ingredient from 5 to 200 mg.

* * * * *